United States Patent
Tang et al.

(10) Patent No.: US 6,620,442 B2
(45) Date of Patent: Sep. 16, 2003

(54) SIMMONDSIN PROCESSING METHODS AND PRODUCTS

(75) Inventors: Qingnong Tang, Saskatoon (CA); James Howard Brown, Scottsdale, AZ (US); Wenhui Fu, Saskatoon (CA)

(73) Assignee: International Flora Technologies, Inc., Gilbert, AZ (US)

( * ) Notice: Subject to any disclaimer, the term of this patent is extended or adjusted under 35 U.S.C. 154(b) by 0 days.

(21) Appl. No.: 09/939,300

(22) Filed: Aug. 24, 2001

(65) Prior Publication Data

US 2003/0044477 A1 Mar. 6, 2003

(51) Int. Cl.$^7$ ............... A61K 35/78; A61K 31/70
(52) U.S. Cl. ............... 424/725; 424/776; 514/23; 514/25; 536/17.9
(58) Field of Search ............... 424/725, 776; 536/17.9; 514/23, 25

(56) References Cited

U.S. PATENT DOCUMENTS

| 4,148,928 A | * | 4/1979 | Sodini et al. |
| 5,672,371 A | * | 9/1997 | D'Oosterlynck |
| 6,007,823 A | * | 12/1999 | Abbott et al. |

FOREIGN PATENT DOCUMENTS

| JP | 02053896 | * | 2/1990 |

OTHER PUBLICATIONS

Van Boven et al. J. Chrom. B: Biomed. Appl. 1994, vol. 655, pp. 281–285.*

* cited by examiner

*Primary Examiner*—Christopher R. Tate
(74) *Attorney, Agent, or Firm*—Hoffmann & Baron, LLP (57) ABSTRACT

The invention provides a process for reducing odor, bitterness, astringency and pungency of a Simmondsins extract by dissolving the Simmondsins extract in a solvent if the Simmondsins extract is in a dry form, reacting the liquid Simmondsins extract with a carbonaceous adsorbent, such as activated carbon, to obtain a mixture, separating the adsorbent from the mixture to obtain a purified liquid extract, and drying the purified liquid extract. The invention also provides a process for preparing a Simmondsins extract having reduced odor, bitterness, astringency and pungency by eluting plant material containing Simmondsins with a polar organic solvent to dissolve the Simmondsins, separating the eluent containing the Simmondsins and the solvent from the plant material to obtain a dilute crude Simmondsins extract, concentrating the crude Simmondsins extract, removing any oils from the concentrated crude Simmondsins extract, and then carrying out the steps for reducing odor, bitterness, astringency and pungency of extract as above. The invention also provides a feed containing a Simmondsins extract having reduced odor, bitterness, astringency and pungency.

25 Claims, 4 Drawing Sheets

| # | Compound Name | Migration Time (min) | Response (mAU) | Concentration (µg/ml) |
|---|---|---|---|---|
| 1 | Simmondsin | 6.073 | 1.322 | $3.085 \times 10^3$ |
| 2 | Didemethyl Simmondsin | 6.648 | 0.446 | $1.765 \times 10^3$ |
| 3 | Simmondsin Ferulate | 10.422 | 0.206 | 393.233 |
| 4 | Gallic Acid (IS) | 20.769 | 0.374 | 200.000 |

Figure 4

| # | Compound Name | Migration Time (min) | Response (mAU) | Concentration (μg/ml) |
|---|---|---|---|---|
| 1 | Simmondsin | 5.830 | 1.033 | $2.208 \times 10^3$ |
| 2 | Didemethyl Simmondsin | 6.337 | 0.280 | $1.016 \times 10^3$ |
| 3 | Simmondsin Ferulate | 0.000 | 0.000 | 0.000 |
| 4 | Gallic Acid (IS) | 18.910 | 0.408 | 200.000 |

SIMMONDSIN PROCESSING METHODS AND PRODUCTS

FIELD OF THE INVENTION

The invention relates to simmondsin extracts, and particularly, to a process of reducing odour, bitterness, astringency and pungency of a simmondsin extract.

BACKGROUND OF THE INVENTION

Jojoba has a unique wax ester oil, which is widely used in cosmetics and lubricants. After oil extraction, the de-fatted and partially de-fatted jojoba meals contain several compounds such as simmondsin and its analogues, phytic acid, trypsin and tannin.

Simmondsins and its analogues are unique components of jojoba and have been the subject of scientific studies for about 30 years. The structures of simmondsins have been elucidated and their chemical properties defined. In this document, the term "Simmondsins" (capitalised, plural) is used to indicate three analogues of simmondsin, which include simmondsin, didemethyl simmondsin and simmondsin ferulate.

An important property of simmondsin and simmondsin ferulate is their reported ability to cause a significant food intake reduction in animals. Didemethyl simmondsin is thought not to have such efficacy. Currently, the reduction of food intake induced by simmondsin and simmondsin ferulate is attributed to the stimulation of satiation, probably through the stimulation of cholecystokinin production (Cokelaere, et al., *Proceedings of the Ninth International Conference on Jojoba and Its Uses and of the Third International Conference on New Industrial Crops and Products,* 135–136, 1996; Flo et al. *Proceedings of the Ninth International Conference on Jojoba and Its Uses and of the Third International Conference on New Industrial Crops and Products,* 135–136, 1996). Simmondsin ferulate is reported to have about 67% efficacy compared to simmondsin in tests involving rats (Cokelaere, et al., 1996). The food intake reduction induced by simmondsin and simmondsin ferulate may be useful in weight control of animals. Simmondsin and simmondsin ferulate may be extracted from jojoba meal, or any other plant containing Simmondsins, and may be used for the purpose of weight control in animals and humans.

Simondsin and its analogues may be extracted with organic solvents (i.e. acetone, methanol, ethanol and ethyl acetate) from de-fatted jojoba meal and purified by chromatographic techniques such as high performance liquid chromatography (Booth et al., *Life Science* 15: 1115–1120, 1974; Verbiscar and Banigan, *Journal of Agricultural and Food Chemistry* 26: 1456–1459, 1987; Dangreau and Cokeraere, Duch Patent No. 8901639, 1991; Van Boven at al., *Journal of Agricultural and Food Chemistry* 41: 1606–1607, 1993; Van Boven at al., *Journal of Agricultural and Food Chemistry* 41: 1118–1121, 1994a; Decuypere and Cokelaere, U.S. Pat. No. 9,425,035, 1994; Van Boven et. al., *Proceedings of the Ninth International Conference on Jojoba and Its Uses and of the Third International Conference on New Industrial Crops and Products,* 135–136, 1996; Abbot at al., U.S. Pat. No. 9,962,530, 1999). However, the technique of high performance liquid chromatography may be too costly to be economically feasible for industrial scale production of simmondsin products.

Erhan et al. (*Industrial Crops and Products* 6: 147–154, 1997) prepared a concentrate of Simmondsins in a pilot scale operation using the technique of water extraction, which was followed by ultrafiltration and spray drying. The final powdery concentrate reportedly contained about 41.3% Simmonsins.

Problematically, crude extracts or concentrates of Simmondsins generated through organic solvent or water extraction of de-fatted jojoba meal may contain odour and bitter components, and may have a strong astringent and pungent taste. Without further purification, the extract of Simmondsins may therefore not be palatable.

SUMMARY OF THE INVENTION

It has now been unexpectedly discovered that simmondsin ferulate may be significantly responsible for the unpalatability of Simmondsins extracts that have been extracted using prior art processes. It has further been unexpectedly discovered that simmondsin ferulate may be selectively reduced or removed from the extracts during the extraction processes, or at any time thereafter, by treatment with a carbonaceous adsorbent, such as activated carbon, in accordance with the processes of the present invention.

In an embodiment of the present invention, there is provided a process for reducing odour, bitterness, astringency or pungency of a Simmondsins extract by dissolving the Simmondsins extract in a solvent (if the Simmondsins extract is in a dry form), reacting the liquid Simmondsins extract with a carbonaceous adsorbent, for example activated carbon, to obtain a mixture, separating the adsorbent from the mixture to obtain a purified liquid extract, and drying the purified liquid extract. A carbonaceous adsorbent is any adsorbent which is comprised of molecules that are made up substantially of carbon atoms and which exhibits adsorbent characteristics like activated carbon.

In another embodiment of the present invention there is provided a process for preparing a Simmondsins extract having improved organoleptic characteristics, for example, reduced odour, bitterness, astringency or pungency, comprising the steps of eluting plant material containing Simmondsins with a polar organic solvent to dissolve the Simmondsins, separating the eluent containing the Simmondsins and the solvent from the plant material to obtain a dilute crude Simmondsins extract, concentrating the crude Simmondsins extract, removing oils from the concentrated crude Simmondsins extract, reacting the concentrated crude Simmondsins extract with a carbonaceous adsorbent to obtain a mixture, separating the adsorbent from the mixture to obtain a purified liquid extract, and drying the purified liquid extract.

In some embodiments, the crude Simmondsins extract may be enriched to increase the total simmondsin content. This may be achieved by extraction with a solvent system of ethanol and ethyl acetate mixture at various ratios.

In an another embodiment, the invention provides a feed containing a Simmondsins extract of the invention.

In alternative embodiments, the purified Simmondsins extract of the invention may be blended into feed as a food intake suppressant.

DETAILED DESCRIPTION OF THE INVENTION

Extraction of a crude Simmondsins extract from plant material containing simmondsin and its analogues may comprise the steps of: extracting Simmondsins from plant material containing Simmondsins with a polar organic solvent, separating insoluble solids from the Simmondsins to obtain a solvent extract, or concentrating and removing solvent from the solvent extract, for example through evaporation or distillation; or removing oil from the Simmondsins extract, for example by gravity separation or centrifugation.

The process may also comprise the step of enriching the crude Simmondsins extract by extraction with a solvent system of ethanol and ethyl acetate mixture at various ratios. The process may also comprise the step of removing the adsorbent from the purified Simmondsins concentrate through filtration.

A crude extract of Simmondsins may be first obtained from plant material containing Simmondsins. The starting material for use in the process of the invention may be any plant material containing Simmondsins. For example, the starting material may be jojoba meal obtained from the physical processing of jojoba plants. The preferred starting material is de-fatted or partially de-fatted jojoba meal. Partially de-fatted jojoba meal typically contains about 6–7% oil while de-fatted jojoba meal typically contains about 0.2–2% oil.

An organic solvent may be used in the extraction of crude Simmondsins extract from the starting material. The organic solvent may, for example, be methanol, ethanol, iso-propanol, or another polar organic solvent with similar characteristics. The organic solvent may be recovered from the crude Simmondsins extract, for example through evaporation or through distillation. The extraction of crude Simmondsins extract with the organic solvent may for example be carried out at a temperature in the range of 4–78° C. for 30–120 minutes. In some embodiments, the preferred temperature may be in the range of 20–40° C. for approximately 60 minutes.

Table 1 shows examples of the relationship between the solvent polarity, the purity of crude extracts and the recovery yields for Simmondsins. The polarity of Simmondsins increases in the order of simmondsin 2-ferulate <simmondsin<didemethyl simmondsin. Because of the degree of their polarity, Simmondsins are typically soluble in polar solvents such as water, methanol and ethanol. The polarity of solvents may be a factor influencing extractability and the purity of the crude Simmondsins extract.

TABLE 1

Effect of solvents on the purity of the crude extracts and the recovery yield of Simmondsins.

| Solvent[b] | Polarity Index[b] | Simmondsins in the Extracts[c] (%) | Recovery Yield of Simmondsins[d] (%) |
| --- | --- | --- | --- |
| Water | 9.0[a] | 36.7 | 74.0 |
| 20% Ethanol | 8.2 | 38.9 | 71.2 |
| 50% Ethanol | 7.1 | 38.6 | 71.6 |
| 75% Ethanol | 6.2 | 43.3 | 77.8 |
| 95% Ethanol | 5.4 | 49.4 | 74.6 |

TABLE 1-continued

Effect of solvents on the purity of the crude extracts and the recovery yield of Simmondsins.

| Solvent[b] | Polarity Index[b] | Simmondsins in the Extracts[c] (%) | Recovery Yield of Simmondsins[d] (%) |
| --- | --- | --- | --- |
| Anhydrous Ethanol | 5.2[a] | 48.0 | 70.7 |
| Methanol | 6.6[a] | 45.6 | 82.1 |
| Acetone | 5.4[a] | 39.0 | 5.7 |
| 75% Iso-propanol | 5.5 | 46.1 | 73.5 |
| 95% Iso-propanol | 4.5 | 49.0 | 68.3 |
| 100% Iso-propanol | 4.3[a] | 32.6 | 6.8 |

[a]The polarity index values for the indicated solvents are obtained from "Solvent Selection via Miscibility Number", Godfrey, Norman B., Chemtech, 1972
[b]The polarity index values of the mixed solvent, e.g. from solvents A & B, was calculated using the values designated as using the values designated with [a], as follows: Polarity of Mixed Solvents A & B = % Solvent A × Polarity A + % Solvent B × Polarity B
[c]Simmondsins were used in this report to indicate simmondsin, didemethyl simmondsin and simmondsin ferulate.
[d]The recovery yield of Simmondsins was calculated by dividing the Simmondsins in the extracts performed in one extraction with the Simmondsins in the starting material (jojoba meal).

Another factor affecting Simmondsins extraction may be attributed to the extent of hydrogen bonding between the solvent molecules and the strength of hydrogen bonding between the solvent and Simmondsins molecules. The pH of protic solvents like water and ethanol may also effect extraction efficiencies.

In some embodiments, the preferred solvents for Simmondsins extraction may be polar solvents that are capable of hydrogen bonding. Water, methanol at various concentrations, ethanol at various concentrations, and iso-propanol at a concentration of 95% or below may be suitable solvents for use in some embodiments of the processes of the invention. Ethanol may be a preferred solvent for Simmondsins extraction in some embodiments of the invention based on the considerations of extraction efficiency, purity of the extract, economy, safety, and environmental impact.

Figure 1:
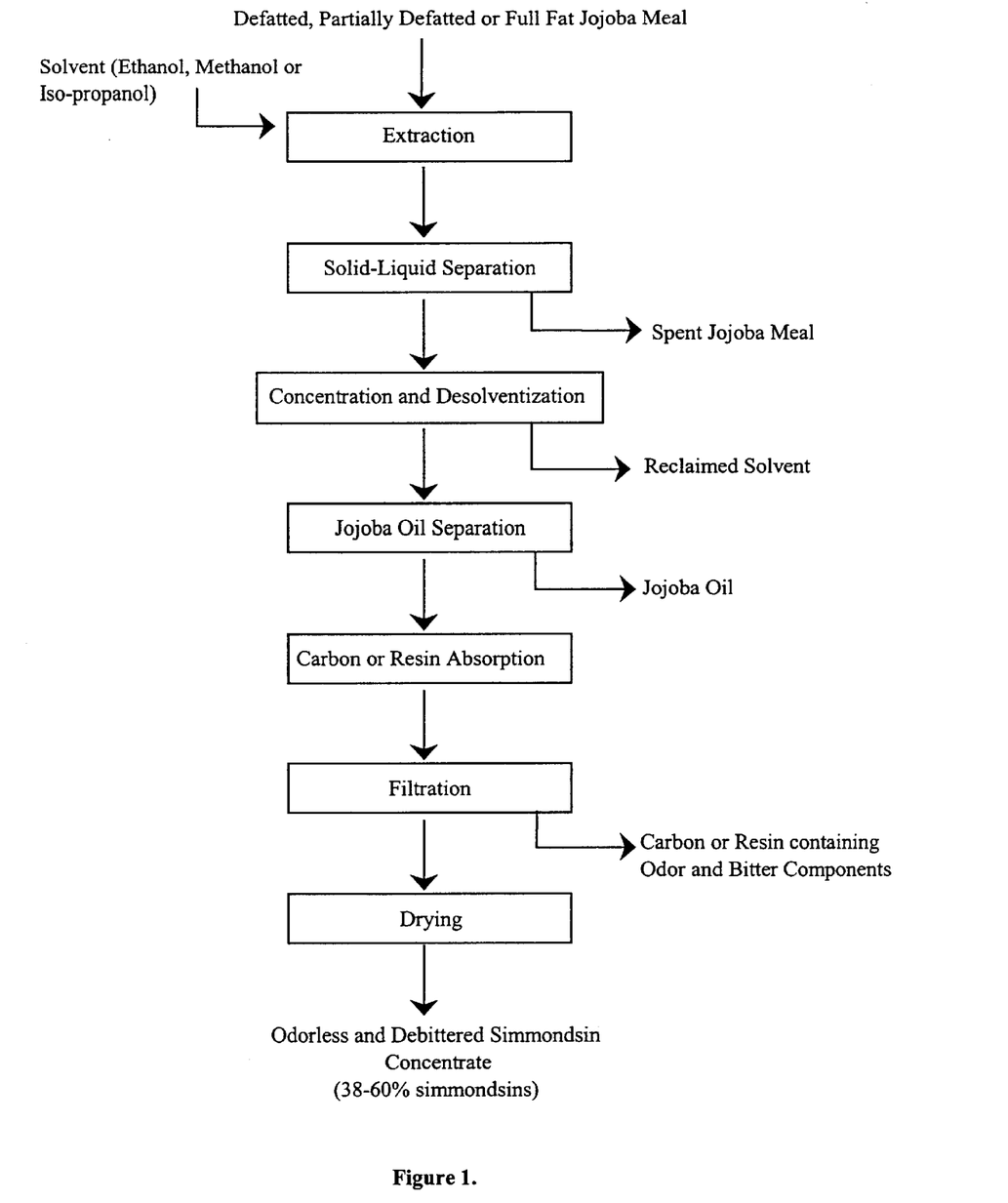
FIG. 1 is a schematic representation of the preparation of purified Simmondsins concentrate from plant materials containing simmondsin and its analogues.

FIG. 1 schematically illustrates the steps of an embodiment of the invention for extracting crude Simmondsins extract from the starting material and purifying the crude Simmondsins extract to remove odour and bitter components as well as simmondsin ferulate. De-fatted or partially de-fatted jojoba meal may be subjected to extraction with various solvents of different concentrations at various temperatures for a varying amount of time. In the extraction process, the jojoba meal may be mixed with the solvent in an extraction vessel (e.g. tank or reactor) by stirring. In some embodiments, the preferred temperature may be room temperature and the preferred amount of contact time between the extract and the solvent may be approximately 120 minutes. One or more extractions may be conducted on the starting material. The number of extractions and the ratio of solvent to solids on a weight to volume basis may affect the recovery yield of Simmondsins. In some embodiments, the increase in extraction temperature from 24 to 100° C. and extraction time from 30 to 120 minutes may have little effect on the recovery yield of Simmondsins. In some embodiments, a recovery yield of Simmondsins in the range of 94–99% may be achieved with three extractions at a solvent to meal ratio of 6 to 1, at an extraction time of 30 minutes or longer, and at room temperature.

The number of extractions and extraction temperature may also affect the purity of the extract. The increase in the number of extractions from 1 to 3 and the extraction temperature from 24 to 100° C. may for example reduce the purity of the extract. In some embodiments, the preferred extraction condition may be at room temperature, 30–120 minute extraction time, 1–3 extractions and a solvent to jojoba meal ratio of 3:1 to 10:1.

After each extraction, the solvent extract containing Simmondsins may be separated from the insoluble solids by conventional solid-liquid separation techniques such as centrifugation with a decanter centrifuge or a basket centrifuge, filtration with a vacuum or pressure filter and gravity separation.

The starting material may be contacted with the solvent in a batch, semi-continuous, or continuous extractor. For semi-continuous and continuous extraction processes, a counter-current or co-current extraction method may be applied. In some embodiments, the extraction of Simmondsins may be achieved by percolation and immersion. For example, Crown solvent extractors, basket extractors and belt extractors are typical extractors that may be used in the extraction of Simmondsins. The contact time for extraction between the jojoba meal and the solvent may for example be in the range of 0.5 to 2 hours. The extraction may be conducted at room temperature, but a higher or lower extraction temperature may also be suitable.

The insoluble solids recovered from the extraction process may be desolventized and dried in a desolventizer and dryer. The dried solids may for example be used as animal feed or as the starting material for preparation of protein concentrate and isolate. The recovered solvent from drying of the solids and concentration of the solvent extract may be re-used in the next batch of the extraction.

The solvent extract containing extracted Simmondsins may be concentrated and desolventized in an evaporator (e.g. rising or falling film evaporators) and/or a distillation unit to remove most of the solvent from the crude extract. The solvent residue in the extract after concentration and desolventization may for example be reduced to the range of 0–5%, and in some embodiments to the range of 0–1%. A phase separation may be conducted after concentration and desolventization. During the phase separation, an oil phase, such as the jojoba oil phase, may be separated from the crude Simmondsins liquid extract, for example by centrifugation with a disc centrifuge or gravity separation.

Figure 2:
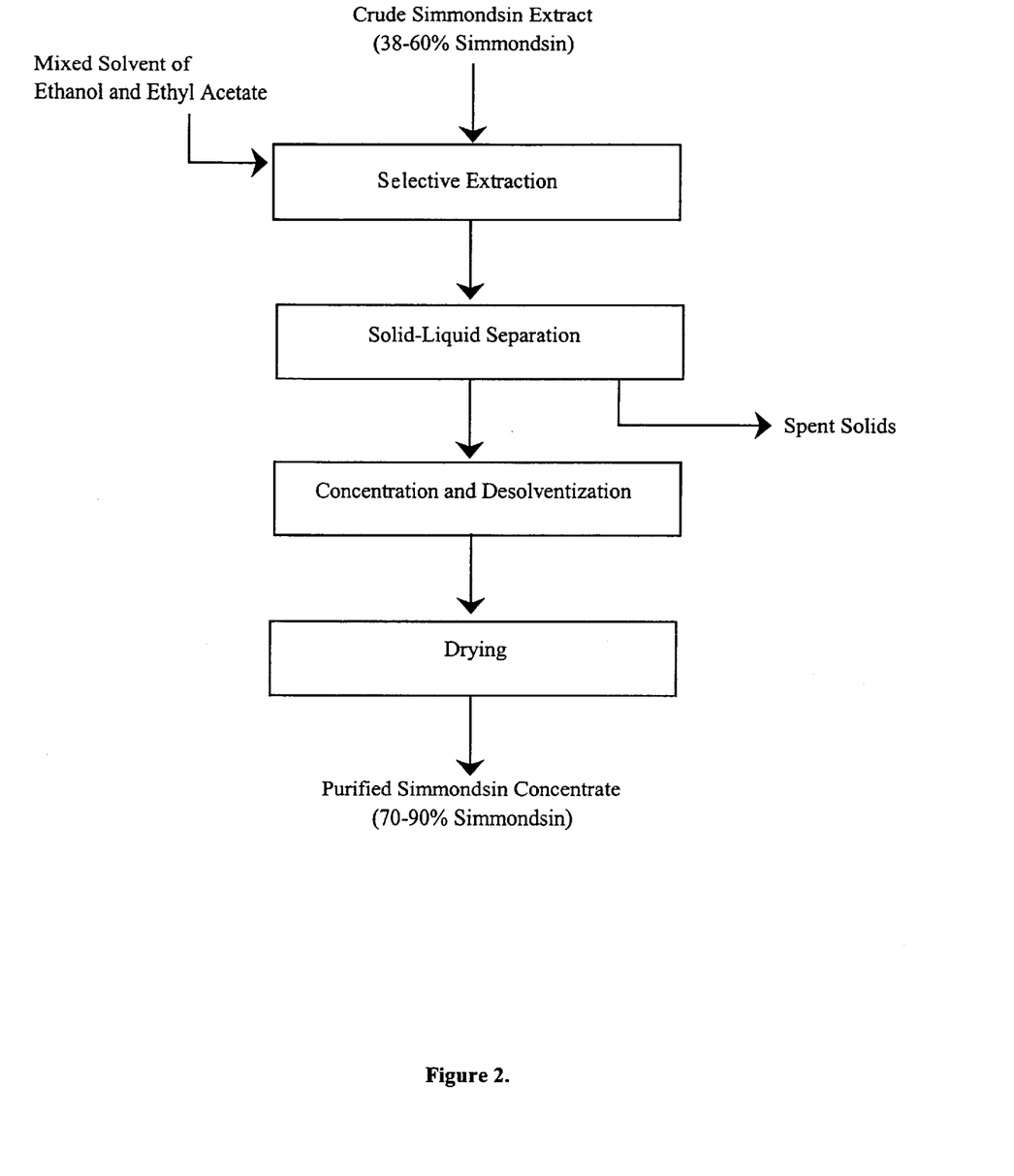
FIG. 2 is a schematic representation of enrichment of crude Simmondsins extract.

In some embodiments, crude Simmondsins extract generated from extraction with organic solvents contains 38–60% total Simmondsins. Such extracts may have a strong odor with bitter, astringent and pungent tastes. It may be possible to reduce the level of some of these impurities by selection of solvents with suitable polarities for use in techniques of solubilization and precipitation. FIG. 2 schematically illustrates a method employed in one embodiment to enrich a crude Simmondsins extract in order to increase the simmondsin content in the extract. The crude Simmondsins extract may for example be enriched by extracting the dried crude extract with a mixed solvent of ethanol and ethyl acetate at various ratios. In some embodiments, the simmondsin content in the extract can be increased to about 70–90% total Simmondsins.

The crude Simmondsins extract produced from the extraction with polar solvents may not be palatable because of its odor, bitterness, and astringent and pungent tastes. For example, in feeding trials, dogs refused to eat any form of dog foods (i.e. liquid, semi-dry and dry blends) formulated with a crude Simmondsins extract.

In some embodiments, crude Simmondsins extract may be treated with a sufficient amount of a carbonaceous adsorbent, such as activated carbon, to remove impurities and some simmondsin ferulate. For example, a crude jojoba extract prepared after removal of a jojoba oil phase may be mixed with activated carbon. The dosage level of the carbon may for example be 5–100% (w/w) based on the dried weight of the extracted solids in the crude extract, or 20–80% (w/w), or a dosage level of 30–60% (w/w). The mixed slurry of activated carbon and crude extract may be vigorously agitated in a tank at 4–80° C. for 10–160 minutes and preferably at 40–60° C. for 30–90 minutes. After carbon treatment, the liquid extract may be separated from the spent solids, for example by filtration or centrifugation. Filtration may be done with a filter press pre-coated with a layer of celite as filter aid. The purified liquid concentrate may be dried by conventional drying methods such as spray drying with a spray dryer, vacuum drying with a vacuum dryer, freeze drying with a freeze dryer, or drum drying with a drum dryer. The dried purified Simmondsins concentrate may be white, odorless, and with little bitterness, astringent or pungent tastes.

In some embodiments, the simmondsin ferulate in the extract may be reduced by treatment with adsorbent, for example being reduced from an original 5–10% (7.94% in one example) to about 0–2% of total Simmondsins depending on the level of adsorbent dosage. In accordance with one aspect of the invention, the astringent and pungent taste of the extract is reduced significantly by the adsorption of simmondsin ferulate on the adsorbent (such as activated carbon). In some embodiments, odor and bitter components are also removed from the extract through adsorption (for example with activated carbon).

Figure 3:
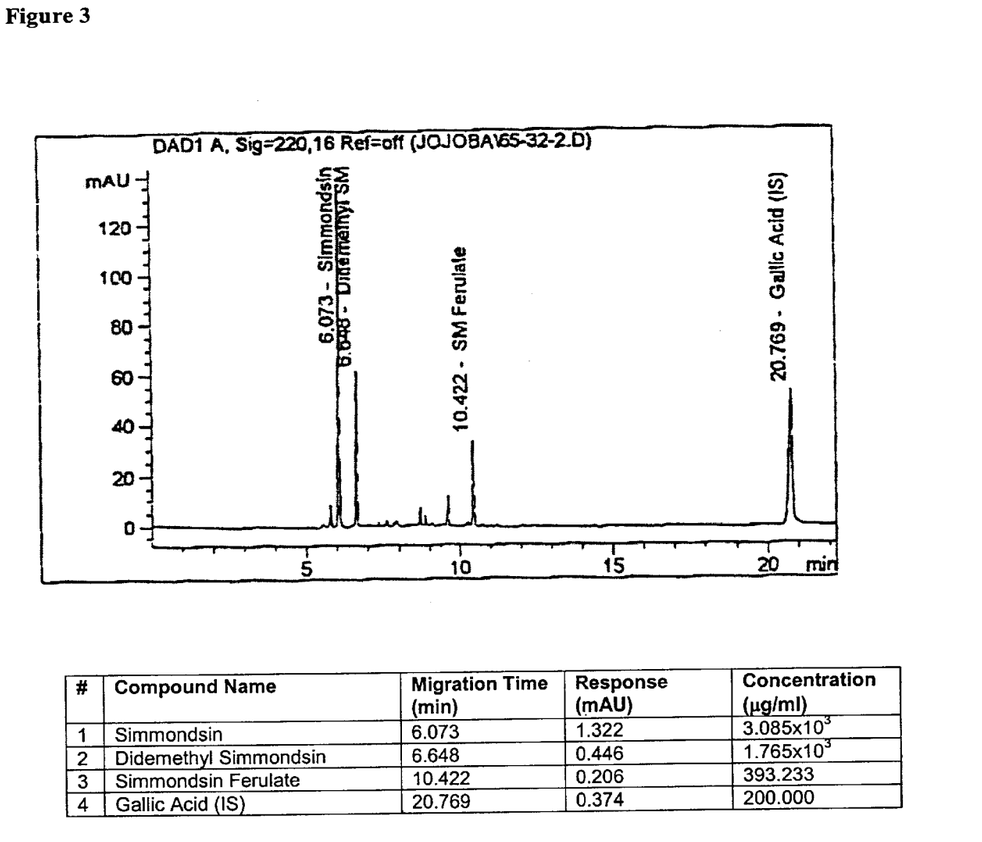
FIG. 3 is an electropherogram of a concentrated crude Simmondsins extract.
Figure 4:
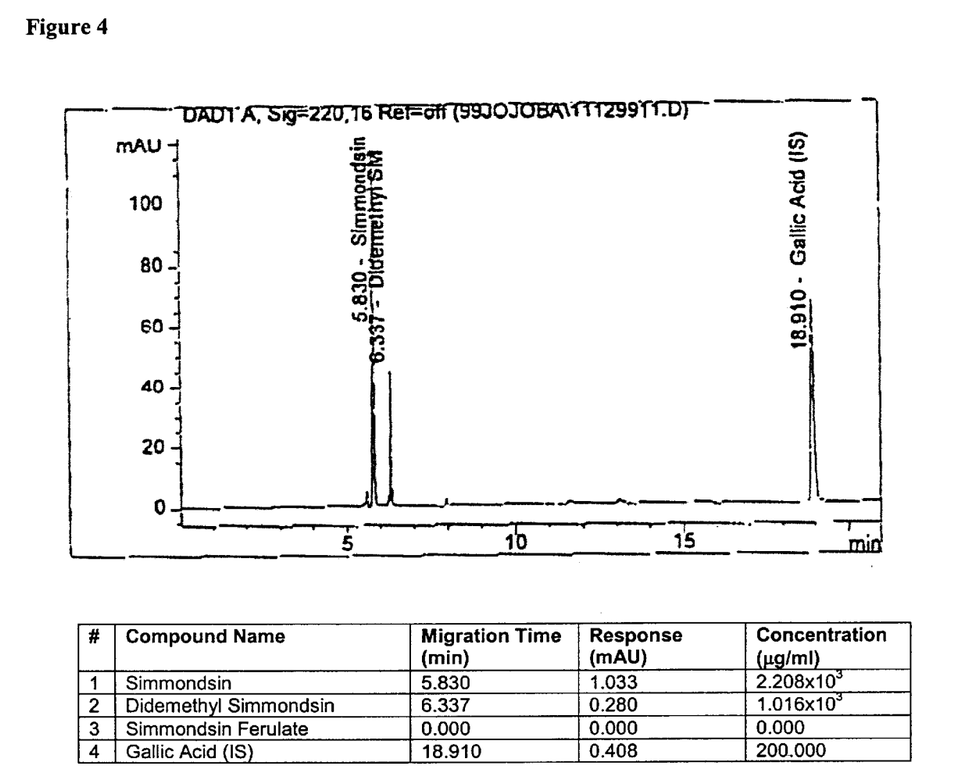
FIG. 4 is a electropherogram of purified Simmondsins concentrate after treatment with activated carbon in accordance with the present invention.

Referring to FIGS. 3 and 4, there are shown electropherograms of a crude Simmondsins extract and a purified Simmondsins concentrate after treatment with activated carbon, respectively, obtained from capillary electrophoresis analyses conducted using gallic acid as the internal standard. Also shown below each graph is a table of the data obtained in the analysis, including: the measured migration time for each compound (in minutes) which is a measure of the time it takes the compound to move from the beginning of the capillary to the detector window; the response (mAU) for each compound which represents the peak area; and the calculated concentration ($\mu$g/ml) of each compound. The first peak in the electropherograms just prior to the simmondsin peak may be the solvent peak. Referring to the electropherogram of the crude Simmondsins extract in FIG. 3, there are shown peaks for simmondsin, didemethyl simmondsin, simmondsin ferulate and gallic acid. In addition, there are a number of peaks for various impurities, distributed between didemethyl simmondsin and simmondsin ferulate, which may be responsible for some of the organoleptic characteristics of the crude Simmondsins extract. Referring to the electropherogram of the purified Simmondsins concentrate after treatment with activated carbon in FIG. 4, there are shown peaks for simmondsin, didemethyl simmondsin, and gallic acid. Noticeably absent are the impurity peaks between the 5 to 10 minute interval, and the peak for simmondsin ferulate.

In some embodiments, an odorless and debittered Simmondsins extract is produced which contains Simmondsins in an amount such as 30%, 40%, 50%, 60%, 70%, 80% or 91% (or any number in between 30% and 91%) Simmondsins by weight of the extract, and in which the amount of simmondsin ferulate is not more than 3% by weight of the extract.

In other embodiments, the invention provides purified Simmondsins concentrates made by the processes of the invention, such as: extracting crude Simmondsins extract from plant material containing simmondsin and its analogues; treating the crude Simmondsins extract with an adsorbent, for example at an elevated temperature, to obtain purified Simmondsins concentrate; and drying said purified Simmondsins concentrate. The purified Simmondsins concentrate herein may also be obtained by alternative processes described.

In some embodiments, the invention provides Simmondsins concentrate for use in the formulation of various foods. The foods may be pet foods such as food for mammals, for example dog food or cat food. The pet food may be dry, semi-dry or liquid pet food. The use of the Simmondsins concentrate may be to influence or reduce the food intake of animals, such as mammals, including dogs or cats.

In another embodiment, the invention provides various food formulations containing purified Simmondsins concentrate. The food formulations may contain 0.1–5% purified Simmondsins concentrate (or simmondsin) based on the weight of pet food. The preferred amount of purified Simmondsins concentrate may be 0.5–2%.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

EXAMPLES

Example 1

Preparation of Purified Simmondsins Concentrate from De-fatted Jojoba Meal

A slurry of jojoba meal was prepared by mixing 3.52 liters of 95% ethanol with 440 g of de-fatted jojoba meal. The de-fatted jojoba meal containing about 0.5–2% residue oil was supplied by International Flora Technologies, Gilbert, Ariz. The slurry was vigorously agitated at room temperature (23° C.) for 2 hours. After extraction the crude extract was separated and recovered from the solids by filtration through a Whatman #4 filter paper. The extraction and solid-liquid separation were repeated twice with 1.32 liters of 95% ethanol as the solvent in each extraction. The crude liquid extracts were pooled together as the combined extract. Ethanol was removed from the combined crude extract by concentrating it to about 14% of its original weight with a laboratory rotary evaporator. A layer of oil was formed on the top of crude extract after concentration, which is removed from the crude extract with a separating funnel.

Approximately 29.3 g of activated carbon from Norit Americas Inc. and marketed under the trade-mark DARCO® KB was added to the crude extract. The particular lot of the DARCO® KB activated carbon used had the following properties as reported by Norit Americas Inc. in a Certificate of Analysis:

| | |
|---|---|
| Moisture, % | 26 |
| Molasses decolorizing efficiency | 230 |
| Water Solubles, % | 0.69 |
| pH | 6.2 |
| Phosphate, % | 0.4 |
| Particle Size (volume %), d5, $\mu$ | 2.7 |
| Particle Size (volume %), d50, $\mu$ | 32 |
| Particle Size (volume %), d95, $\mu$ | 100 |

The slurry was vigorously agitated at 60–65° C. for 1 hour. After carbon treatment the purified Simmondsins concentrate was separated from the spent carbon by filtering it through a Whatman #4 filter paper with 2.3 g of celite as filter aid. The carbon treated extract was concentrated to 50% of its original weight, which was followed by drying with a vacuum tray dryer at 50° overnight. Approximately 76 g of the purified Simmondsins concentrate containing 5% moisture were produced. The average recovery yield of simmondsin and its analogues obtained from three extractions as described was about 81.6% and the purity of the purified Simmondsins concentrate was about 58.52%. The purified Simmondsins concentrate contained about 36.96% simmondsin, 20.60% didemethyl simmondsin and 0.96% simmondsin ferulate. The purified Simmondsins concentrate had reduced odor, bitterness, astringency, and pungency.

Example 2

Preparation of Purified Simmondsins Concentrate from Partially De-fatted Jojoba Meal The processing procedure was the same as that of Example 1. The starting material was the partially de-fatted jojoba meal, which was generated from the full pressing of jojoba seeds. The composition of the purified Simmondsins concentrate and the total recovery yield of simmondsin and its analogues were similar to those of Example 1. The purified Simmondsins concentrate had reduced odor, bitterness, astringency, and pungency.

Example 3

Preparation of Purified Simmondsins Concentrate from De-fatted Jojoba Meal

The processing procedure was the same as that of Example 1 except that methanol was used as the extraction solvent. The average recovery yield of simmondsin and its analogues obtained from three extractions as described was about 92.5%. The purity of Simmondsins concentrate was about 54.0%. The purified Simmondsins concentrate had reduced odor, bitterness, astringency, and pungency.

Example 4

Preparation of Purified Simmondsins Concentrate from De-fatted Jojoba Meal

The processing procedure was the same as that of Example 1 except that 75% iso-propanol was used as the extraction solvent. The average recovery yield of simmondsin and its analogues obtained from three extractions as described about 82.76%. The purity of Simmondsins concentrate was about 54.6%. The purified Simmondsins concentrate had reduced odor, bitterness, astringency, and pungency.

Example 5

Preparation of Purified Simmondsins Concentrate from De-fatted Jojoba Meal

The processing procedure was the same as that of Example 1 except that water was used as the extraction solvent. The average recovery yield of simmondsin and its analogues obtained from three extractions as described was about 83.32%. The purity of Simmondsins concentrate was about 43.5%. The purified Simmondsins concentrate had reduced odor, bitterness, astringency, and pungency.

Example 6

Enrichment of Purified Simmondsins Concentrate

Example 1 was repeated and the purified Simmondsins concentrate was enriched to increase its purity. Approximately 76 g of the purified Simmondsins concentrate containing 58.52% total Simmondsins were milled into powder with a laboratory pin mill. The milled Simmondsins concentrate was mixed with 760 ml of solvent containing ethyl acetate and absolute ethanol at a volume ratio of 4 to 1. The slurry was refluxed at the boiling point for 1 hour before cooling and filtering through Whatman #4 filter paper to separate the extract from the solid residues. The solid residues were further subjected to extraction by refluxing twice with 380 ml of the same solvent system. The extracts were recovered by solid-liquid separation through filtration with a Whatman #4 filter paper. The combined extract was concentrated and dried by evaporation at a reduced pressure with a laboratory rotary evaporator. The purity of the enriched Simmondsins concentrate was about 84.9%. The enriched Simmondsins concentrate was odorless and without bitterness or astringent and pungent taste. The enriched Simmondsins concentrate contained 69.4% simmondsin, 14.5% didemethyl simmondsin, 1% simmondsin 2-ferulate, and 2.6% moisture.

Example 7

Influence of Simmondsins Concentrate on the Food Intake Reduction and Body Weight Loss of Dogs Ten health adult dogs, three females and seven males were individually identified, underwent physical examinations and were randomly divided into two groups. Physical examination included examination by a veterinarian, CBC, blood profile and electrolytes. Measurements of body weights, Body Condition Score (BCS), pelvic circumference and hock to stifle length were recorded. None of the animals were pregnant or lactating. All animals were residents of and provided by the Ontario Nutri-Lab (ONL) of Fergus, Ontario, Canada and were individually housed according to USDA standard practices. All animals were currently vaccinated.

A semi-dry dog food was prepared by mixing canned dog food with other ingredients. Half of the dog food was used as the control diet that was fed to a control group of 5 dogs once a day for a testing period of 4 weeks. The other half of the dog food was formulated with purified Simmondsins concentrate powder at a simmondsin concentration in the dog food of about 1% by weight. The Simmondsins formulated dog food was used as the test diet that was fed to a test group of 5 dogs once a day for a testing period of 4 weeks. Initial feeding evaluation showed that the dogs did not have any preference between the control and test diet, indicating the test diet formulated with the purified Simmondsins concentrate was as palatable as the control diet. The four week trial resulted in a statistically significantly decrease in food intake and weight loss in the test group when compared to the control group. The Body Condition Score (BCS) changed and fat levels decreased in the dogs of test group when compared to the dogs of control group.

What is claimed is:

1. A process comprising the steps of:
   a) dissolving a dry Simmondsins extract in a solvent to form a liquid Simmondsins extract;
   b) reacting the liquid Simmondsins extract with a carbonaceous adsorbent to obtain a mixture;
   c) separating the carbonaceous adsorbent from the mixture to obtain a purified liquid Simmondsins extract; and
   d) drying the purified liquid Simmondsins extract.

2. The process of claim 1 wherein the adsorbent is activated carbon.

3. The process of claim 2 further comprising the step of agitating the mixture during the reaction of the liquid Simmondsins extract and adsorbent.

4. The process of claim 3 wherein the amount of adsorbent reacted with the Simmondsins extract is within an approximate range of 5% to 100% of the dry weight of the Simmondsins extract.

5. The process of claim 4 wherein the reaction of the liquid Simmondsins extract and adsorbent is carried out at a temperature in a range of 4° C. to 80° C.

6. The process of claim 5 wherein the mixture is agitated for a period of time between 10 minutes to 160 minutes.

7. The process of claim 3 wherein the amount of adsorbent reacted with the Simmondsins extract is within an approximate range of 20% to 80% of the dry weight of the Simmondsins extract.

8. The process of claim 7 wherein the reaction of the liquid Simmondsins extract and adsorbent is carried out at a temperature in a range of 40° C. to 60° C.

9. The process of claim 8 wherein the mixture is agitated for a period of time between 30 minutes to 90 minutes.

10. The process of claim 1, wherein the process alters an organoleptic characteristic of the Simmondsins extract, wherein the organoleptic characteristic is selected from the group consisting of odour, bitterness, astringency and pungency.

11. A process comprising the steps of:
    a) eluting plant material containing Simmondsins with a polar organic solvent to dissolve the Simmondsins to produce an eluent containing the Simmondsins;
    b) separating the eluent containing the Simmondsins from the plant material to obtain a crude Simmondsins extract;
    c) reacting the crude Simmondsins extract with a carbonaceous adsorbent to obtain an adsorbent mixture; and
    d) separating the adsorbent from the adsorbent mixture to obtain a liquid Simmondsins extract.

12. The process of claim 11 wherein the adsorbent is activated carbon.

13. The process of claim 12 further comprising after step b) and before step c) concentrating and removing oils from the crude Simmondsins extract.

14. The process of claim 13 further comprising the step of agitating the mixture during the reaction of the liquid Simmondsins extract and adsorbent.

15. The process of claim 14 wherein the amount of adsorbent reacted with the Simmondsins extract is within an approximate range of 5% to 100% of the dry weight of the Simmondsins extract.

16. The process of claim 15 wherein the reaction of the liquid Simmondsins extract and adsorbent is carried out at a temperature in a range of 4° C. to 80° C.

17. The process of claim 16 wherein the mixture is agitated for a period of time between 10 minutes to 160 minutes.

18. The process of claim 14 wherein the amount of adsorbent reacted with the Simmondsins extract is within an approximate range of 20% to 80% of the dry weight of the Simmondsins extract.

19. The process of claim 18 wherein the reaction of the liquid Simmondsins extract and adsorbent is carried out at a temperature in a range of 40° C. to 60° C.

20. The process of claim 19 wherein the mixture is agitated for a period of time between 30 minutes to 90 minutes.

21. The process of claim 11 further comprising after step b) and before step c) mixing the crude Simmondsins extract with a solvent comprising at least one of ethanol and ethyl acetate.

22. The process of claim 21 wherein the adsorbent is activated carbon.

23. The process of claim 22 further comprising the step of agitating the mixture during the reaction of the liquid Simmondsins extract and adsorbent.

24. The process of claim 23 wherein reaction of the liquid Simmondsins extract and adsorbent is carried out at a temperature in a range of 4° C. to 80° C.

25. The process of claim 24 wherein the amount of adsorbent reacted with the Simmondsins extract is within an approximate range of 5% to 100% of the dry weight of the crude Simmondsins extract.

* * * * *